US011712289B2

(12) United States Patent
Sartor

(10) Patent No.: US 11,712,289 B2
(45) Date of Patent: Aug. 1, 2023

(54) VESSEL-SEALING DEVICE INCLUDING FORCE-BALANCE INTERFACE AND ELECTROSURGICAL SYSTEM INCLUDING SAME

(71) Applicant: Covidien LP, Mansfield, MA (US)

(72) Inventor: Joe D. Sartor, Longmont, CO (US)

(73) Assignee: Covidien LP, Mansfield, MA (US)

( * ) Notice: Subject to any disclaimer, the term of this patent is extended or adjusted under 35 U.S.C. 154(b) by 432 days.

(21) Appl. No.: 17/086,811

(22) Filed: Nov. 2, 2020

(65) Prior Publication Data

US 2021/0045803 A1 Feb. 18, 2021

Related U.S. Application Data

(63) Continuation of application No. 14/843,297, filed on Sep. 2, 2015, now Pat. No. 10,820,939.
(Continued)

(51) Int. Cl.
*A61B 18/14* (2006.01)
*A61B 18/00* (2006.01)
*A61B 90/00* (2016.01)

(52) U.S. Cl.
CPC ...... *A61B 18/1445* (2013.01); *A61B 18/1447* (2013.01); *A61B 2018/0063* (2013.01);
(Continued)

(58) Field of Classification Search
CPC ............ A61B 18/1445; A61B 18/1447; A61B 2018/0063; A61B 2018/0091; A61B 2018/1455; A61B 2090/064
See application file for complete search history.

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 Y 9/2009
DE 2415263 A1 10/1975
(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003, 4 pages.
(Continued)

*Primary Examiner* — Michael F Peffley
*Assistant Examiner* — Bo Ouyang
(74) *Attorney, Agent, or Firm* — Carter, DeLuca & Farrell LLP

(57) ABSTRACT

A surgical instrument includes a housing having a shaft affixed thereto, a reciprocatable drive rod slideably disposed at least partially within the shaft, and a force applicator coupled to the drive rod. The shaft includes first and second jaw members attached to a distal end thereof, at least one of which movable relative to the other from a first position wherein the jaw members are disposed in spaced relation relative to one another to at least a second position closer to one another wherein the jaw members cooperate to grasp tissue therebetween. The force applicator and the drive rod mechanically communicate to impart movement to at least one of the jaw members. The bipolar forceps includes a handle assembly and a force-balance interface. The force-balance interface configured to translate a multiple of the user-applied force exerted on the handle assembly into the jaw members.

19 Claims, 8 Drawing Sheets

Related U.S. Application Data

(60) Provisional application No. 62/050,496, filed on Sep. 15, 2014.

(52) U.S. Cl.
CPC ............... *A61B 2018/0091* (2013.01); *A61B 2018/1455* (2013.01); *A61B 2090/064* (2016.02)

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,385,509 B2 | 5/2002 | Das et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| 6,817,973 B2 | 11/2004 | Merril et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 8,613,230 B2 | 12/2013 | Blumenkranz et al. |
| 10,820,939 B2 | 11/2020 | Sartor |
| 2010/0016855 A1 | 1/2010 | Ramstein et al. |
| 2010/0071920 A1* | 3/2010 | Lau ................ B25F 5/00 173/1 |
| 2010/0198220 A1 | 8/2010 | Boudreaux et al. |
| 2011/0306471 A1 | 12/2011 | Huang |
| 2012/0172873 A1 | 7/2012 | Artale et al. |
| 2013/0041368 A1 | 2/2013 | Cunningham et al. |
| 2013/0138118 A1 | 5/2013 | Doyle |
| 2014/0005682 A1 | 1/2014 | Worrell et al. |
| 2015/0005768 A1 | 1/2015 | Sutherland et al. |
| 2015/0209059 A1* | 7/2015 | Trees ............... A61B 18/1445 606/205 |

FOREIGN PATENT DOCUMENTS

| | | |
|---|---|---|
| DE | 32514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| JP | 61501068 A | 5/1986 |
| JP | 1024051 A | 1/1989 |
| JP | 1147150 A | 6/1989 |
| JP | 55106 | 1/1993 |
| JP | 0540112 | 2/1993 |
| JP | 0006030945 | 2/1994 |
| JP | 6121797 A | 5/1994 |
| JP | 6285078 A | 10/1994 |
| JP | 06343644 | 12/1994 |
| JP | 6511401 | 12/1994 |
| JP | 07265328 | 10/1995 |
| JP | 856955 | 5/1996 |
| JP | 08252263 A | 10/1996 |
| JP | 8289895 A | 11/1996 |
| JP | 8317934 A | 12/1996 |
| JP | 8317936 A | 12/1996 |
| JP | 910223 A | 1/1997 |
| JP | 09000538 A | 1/1997 |
| JP | 9122138 A | 5/1997 |
| JP | 0010000195 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | 11244298 | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001003400 A | 1/2001 |
| JP | 2001008944 A | 1/2001 |
| JP | 2001029355 | 2/2001 |
| JP | 2001029356 A | 2/2001 |
| JP | 2001128990 A | 5/2001 |

(56) References Cited

FOREIGN PATENT DOCUMENTS

| | | |
|---|---|---|
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | 6502328 B2 | 4/2019 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |

OTHER PUBLICATIONS

Chung et al., "Clinical Experience of Sutureless Closed Hemorrhoidectomy with LigaSure" Diseases of the Colon & Rectum vol. 46, No. Jan. 1, 2003, pp. 87-92.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003, 1 page.
Peterson et al. "Comparison of Healing Process Following Ligation with Sutures and Bipolar Vessel Sealing" Surgical Technology International (2001). (8 pages).
"Electrosurgery: A Historical Overview" Innovations in Electrosurgery; Sales/Product Literature; Dec. 31, 2000, 6 pages.
Johnson et al. "Evaluation of a Bipolar Electrothermal Vessel Sealing Device in Hemorrhoidectomy" Sales/Product Literature; Jan. 2004, 1 page.
E. David Crawford "Evaluation of a New Vessel Sealing Device in Urologic Cancer Surgery" Sales/Product Literature 2000, 1 page.
Johnson et al. "Evaluation of the LigaSure Vessel Sealing System in Hemorrhoidectormy" American College of Surgeons (ACS) Clinicla Congress Poster (2000), 1 page.
Muller et al., "Extended Left Hemicolectomy Using the LigaSure Vessel Sealing System" Innovations That Work, Sep. 1999. (4 pages).
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Nork, Jun. 2002, 4 pages.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report" Innovations That Work, Feb. 2002, 4 pages.

Koyle et al., "Laparoscopic Palomo Varicocele Ligation in Children and Adolescents" Pediatric Endosurgery & Innovative Techniques, vol. 6, No. 1, 2002, pp. 15-19.
W. Scott Helton, "LigaSure Vessel Sealing System: Revolutionary Hemostasis Product for General Surgery"; Sales/Product Literature 1999, 1 page.
LigaSure Vessel Sealing System, the Seal of Confidence in General, Gynecologic, Urologic, and Laparaoscopic Surgery; Sales/Product Literature; Apr. 2002, 8 pages.
Joseph Ortenberg "LigaSure System Used in Laparoscopic 1st and 2nd Stage Orchiopexy" Innovations That Work, Nov. 2002, 4 pages.
Sigel et al., "The Mechanism of Blood Vessel Closure by High Frequency Electrocoagulation" Surgery Gynecology & Dbstetrics, Oct. 1965 pp. 823-831.
Sampayan et al., "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001, 8 pages.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003, pp. 147-151.
"Reducing Needlestick Injuries in the Operating Room" Sales/Product Literature 2001. (1 page).
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001, 1 page.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003, 15 pages.
Dulemba et al. "Use of a Bipolar Electrothermal Vessel Sealer in Laparoscopically Assisted Vaginal Hysterectomy" Sales/Product Literature; Jan. 2004, 1 page.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000, 1 page.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000, 4 pages.
Levy et al. "Use of a New Energy-based Vessel Ligation Device During Vaginal Hysterectomy" Int'l Federation of Gynecology and Obstetrics (FIGO) World Congress 1999, 1 page.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000, 1 page.
Jarrett et al., "Use of the LigaSure Vessel Sealing System for Peri-Hilar Vessels in Laparoscopic Nephrectomy" Sales/Product Literature 2000, 1 page.

(56) References Cited

OTHER PUBLICATIONS

Crouch et al. "A Velocity-Dependent Model for Needle Insertion in Soft Tissue"; Miccai 2005 LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C., 1 page.
McLellan et al. "Vessel Sealing for Hemostasis During Gynecologic Surgery" Sales/Product Literature 1999, 1 page.
Heniford et al. "Initial Research and Clinical Results with an Electrothermal Bipolar Vessel Sealer" Oct. 1999. (1 page).

* cited by examiner

VESSEL-SEALING DEVICE INCLUDING FORCE-BALANCE INTERFACE AND ELECTROSURGICAL SYSTEM INCLUDING SAME

CROSS REFERENCE TO RELATED APPLICATIONS

This application is a continuation of U.S. patent application Ser. No. 14/843,297, filed on Sep. 2, 2015, which claims the benefit of and priority to U.S. Provisional Patent Application Ser. No. 62/050,496, filed on Sep. 15, 2014, the entire disclosures of each of which are incorporated by reference herein.

BACKGROUND

Technical Field

The present disclosure relates to surgical instruments. More particularly, the present disclosure relates to vessel-sealing devices including force-balance interfaces and electrosurgical systems including the same.

Background of Related Art

Electrosurgical instruments have become widely used by surgeons. Electrosurgery involves the application of electrical energy and/or electromagnetic energy to cut, dissect, ablate, coagulate, cauterize, seal or otherwise treat biological tissue during a surgical procedure. Electrosurgery is typically performed using an electrosurgical generator operable to output energy and a handpiece including a surgical instrument (e.g., end effector) adapted to transmit energy to a tissue site during electrosurgical procedures. Electrosurgery can be performed using either a monopolar or a bipolar instrument.

The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue. In monopolar electrosurgery, a patient return electrode, also called a grounding pad, bovie pad, neutral electrode or patient plate, is attached externally to the patient (e.g., a plate positioned on the patient's thigh or back) as the means to complete the electrical circuit between the electrosurgical generator and the patient. When the electrosurgical energy is applied, the energy travels from the active electrode, to the surgical site, through the patient and to the return electrode. In bipolar electrosurgery, both the active electrode and return electrode functions are performed at the site of surgery. Bipolar electrosurgical devices include two electrodes of opposite polarity that are located in proximity to one another for the application of current between their surfaces. Bipolar electrosurgical current travels from one electrode, through the intervening tissue to the other electrode to complete the electrical circuit, thereby eliminating the need for a remotely-located current return. Bipolar instruments generally include end-effectors, such as grippers, cutters, forceps, dissectors and the like.

Forceps utilize mechanical action to constrict, grasp, dissect and/or clamp tissue. By utilizing an electrosurgical forceps, a surgeon can utilize both mechanical clamping action and electrosurgical energy to effect hemostasis by heating the tissue and blood vessels to cauterize, coagulate/desiccate, seal and/or divide tissue. Bipolar electrosurgical forceps utilize two generally opposing electrodes that are operably associated with the inner opposing surfaces of an end effector and that are both electrically coupled to an electrosurgical generator. In bipolar forceps, the end-effector assembly generally includes opposing jaw assemblies pivotably mounted with respect to one another. In bipolar configuration, only the tissue grasped between the jaw assemblies is included in the electrical circuit.

By utilizing an electrosurgical forceps, a surgeon can cauterize, coagulate/desiccate and/or seal tissue and/or simply reduce or slow bleeding by controlling the intensity, frequency and duration of the electrosurgical energy applied through the jaw assemblies to the tissue. Tissue or vessel sealing is a process of liquefying the collagen, elastin and ground substances in the tissue so that they reform into a fused mass with significantly-reduced demarcation between the opposing tissue structures. Cauterization involves the use of heat to destroy tissue and coagulation is a process of desiccating tissue wherein the tissue cells are ruptured and dried.

Since tissue sealing procedures involve more than simply cauterizing tissue, to create an effective seal the procedures involve precise control of a variety of factors. During the sealing process, mechanical factors such as the pressure applied between opposing jaw assemblies and the gap distance between the electrically-conductive tissue-contacting surfaces (electrodes) of the jaw assemblies play a role in determining the resulting thickness of the sealed tissue and effectiveness of the seal.

A variety of types of end-effector assemblies have been employed for various types of electrosurgery using a variety of types of monopolar and bipolar electrosurgical instruments. Electrosurgical instruments may include a movable handle and a drive assembly adapted to impart movement to one or more components of the end-effector assemblies. The movable handle may have a form that fits limited hand sizes.

SUMMARY

The handles on surgical instruments, such as vessel-sealing devices, often are challenging to design in a manner that enables the surgeon to easily apply the required force to optimize the sealing function in coordination with the bipolar electrical current. The handles may limit movement as they may interfere with other instruments or the table or the abdomen of the patient. Further complicating the user interface are the preloaded springs which are often used to fix the tissue compression to a predetermined pressure when the handles are fully closed. This may also result in greater handle movement than is needed to fully operate the jaw members.

According to an aspect of the present disclosure, a surgical instrument is provided that includes a handle assembly, a shaft, an end-effector assembly including opposing jaw members, and a powered force applicator. Jaw movement and jaw closure force are applied by the powered force applicator. The handle assembly is configured to transmit a signal indicative of a force exerted on the handle assembly, e.g., based on a small amount of actual movement of the handle assembly, which is transmitted to the powered force applicator. Force applied by the powered force applicator via the shaft to the jaw members is a multiple of the force exerted on the handle assembly.

According to another aspect of the present disclosure, while energy is applied through the jaw members to tissue, the force applied to the tissue is controlled only by the powered force applicator in order to assure a correct relationship between the intensity, frequency and duration of the energy applied through the jaw members to the tissue, and tissue pressure necessary to effect a proper and effective tissue seal.

According to another aspect of the present disclosure, a surgical instrument is provided that includes a housing having a shaft affixed thereto, a reciprocatable drive rod slideably disposed at least partially within the shaft, and a force applicator coupled to the drive rod. The shaft includes first and second jaw members attached to a distal end thereof, at least one of which movable relative to the other from a first position wherein the jaw members are disposed in spaced relation relative to one another to at least a second position closer to one another wherein the jaw members cooperate to grasp tissue therebetween. The force applicator and the drive rod mechanically communicate to impart movement to one or both of the jaw members. The surgical instrument includes a handle assembly and a force-balance interface. The force-balance interface is configured to translate a multiple of the user-applied force exerted on the handle assembly into the jaw members.

According to another aspect of the present disclosure, an electrosurgical system is provided. The electrosurgical system includes an electrosurgical energy source and an electrosurgical instrument operably coupled to the electrosurgical energy source. The electrosurgical instrument includes a housing having a shaft affixed thereto, a reciprocatable drive rod slideably disposed at least partially within the shaft, and a force applicator coupled to the drive rod. The shaft includes an end-effector assembly wherein the force applicator and the drive rod mechanically communicate to impart movement to the end-effector assembly. The electrosurgical instrument includes a handle assembly and a first force-balance interface. The handle assembly is disposed in association with the housing. The first force-balance interface configured to translate a multiple of the user-applied force exerted on the handle assembly into the end-effector assembly.

In any of the aspects, the force applicator may include electrical, pneumatic, and/or hydraulic components configured to exert a force on the drive rod which results in movement and/or increasing pressure between the jaw members.

BRIEF DESCRIPTION OF THE DRAWINGS

Objects and features of the presently-disclosed force-balance interfaces for use in surgical instruments, such as vessel-sealing devices, e.g., bipolar forceps, and electrosurgical systems including the same will become apparent to those of ordinary skill in the art when descriptions of various embodiments thereof are read with reference to the accompanying drawings, of which.

DETAILED DESCRIPTION

Figure 1:
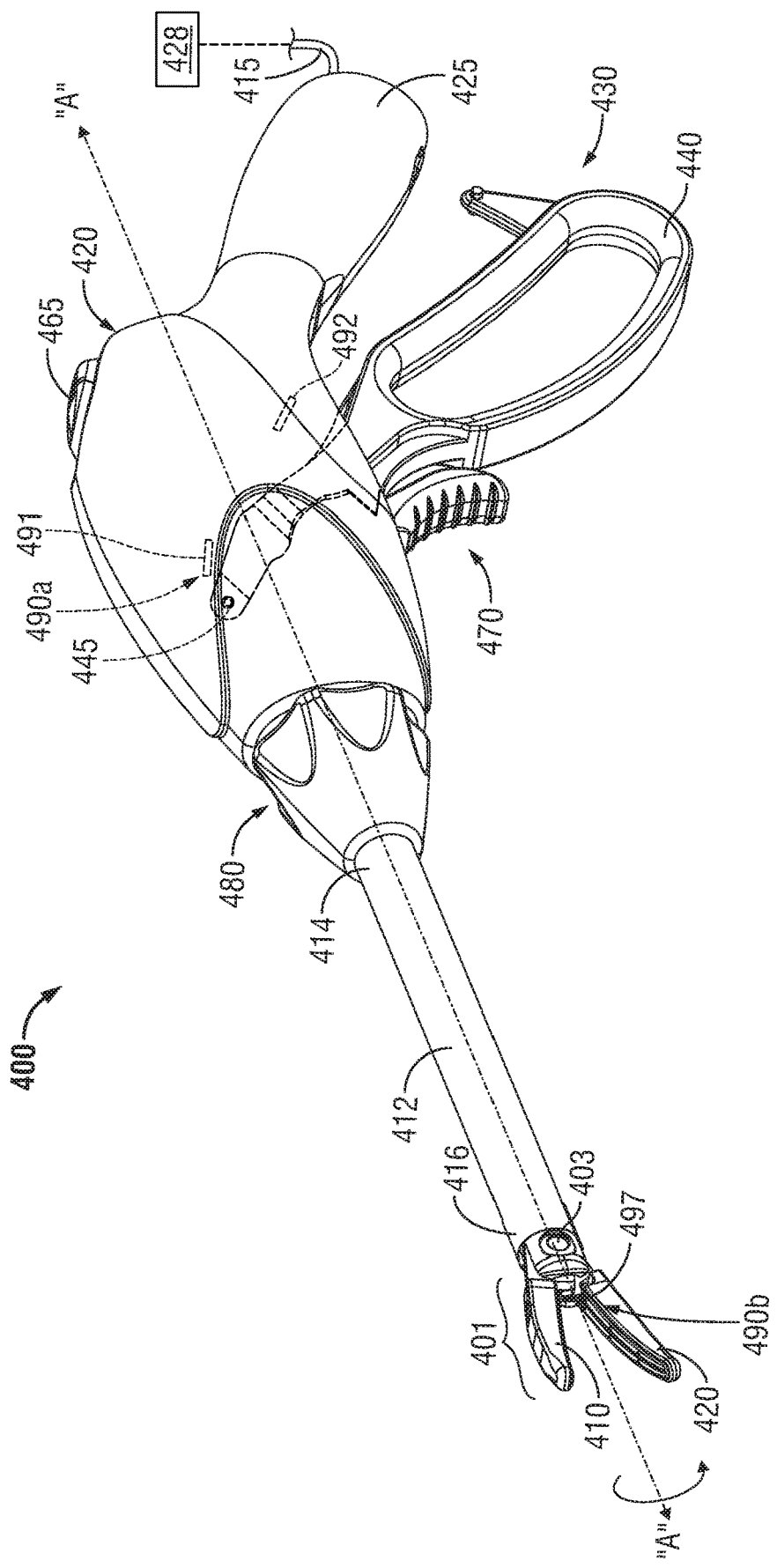
FIG. 1 is a perspective view, partially shown in phantom lines, of a bipolar forceps shown in an open configuration and including a handle assembly and a force-balance interface in accordance with an embodiment of the present disclosure.

Hereinafter, embodiments of a force-balance interface for use in surgical instruments, such as vessel-sealing devices, e.g., bipolar forceps, and electrosurgical systems including the same of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

Various embodiments of the present disclosure provide surgical instruments including a force-balance interface. Various embodiments of the present disclosure provide surgical instruments suitable for sealing, cauterizing, coagulating, desiccating, cutting, and/or dissecting vessels and vascular tissue. Various embodiments of the present disclosure provide an bipolar forceps including a force-balance interface and an end-effector assembly including two jaw members disposed in opposing relation relative to one another. Embodiments of the presently-disclosed bipolar forceps including a force-balance interface may be suitable for utilization in endoscopic surgical procedures, and/or suitable for utilization in open surgical applications.

Embodiments of the presently-disclosed surgical instruments including a force-balance interface may be implemented using a variety of types of energy, e.g., electrosurgical energy at radio frequencies (RF) or at other frequencies, ultrasonic, optical, and/or thermal energy. Embodiments of the presently-disclosed surgical instruments may be connected through a suitable bipolar cable to a generator and/or other suitable power source. Although the following description describes the use of a bipolar forceps, the teachings of the present disclosure may also apply to a variety of surgical devices with an end-effector assembly and including a handle assembly and other components which mutually cooperate to impart movement to one or more components of the end-effector assembly.

Figure 2:
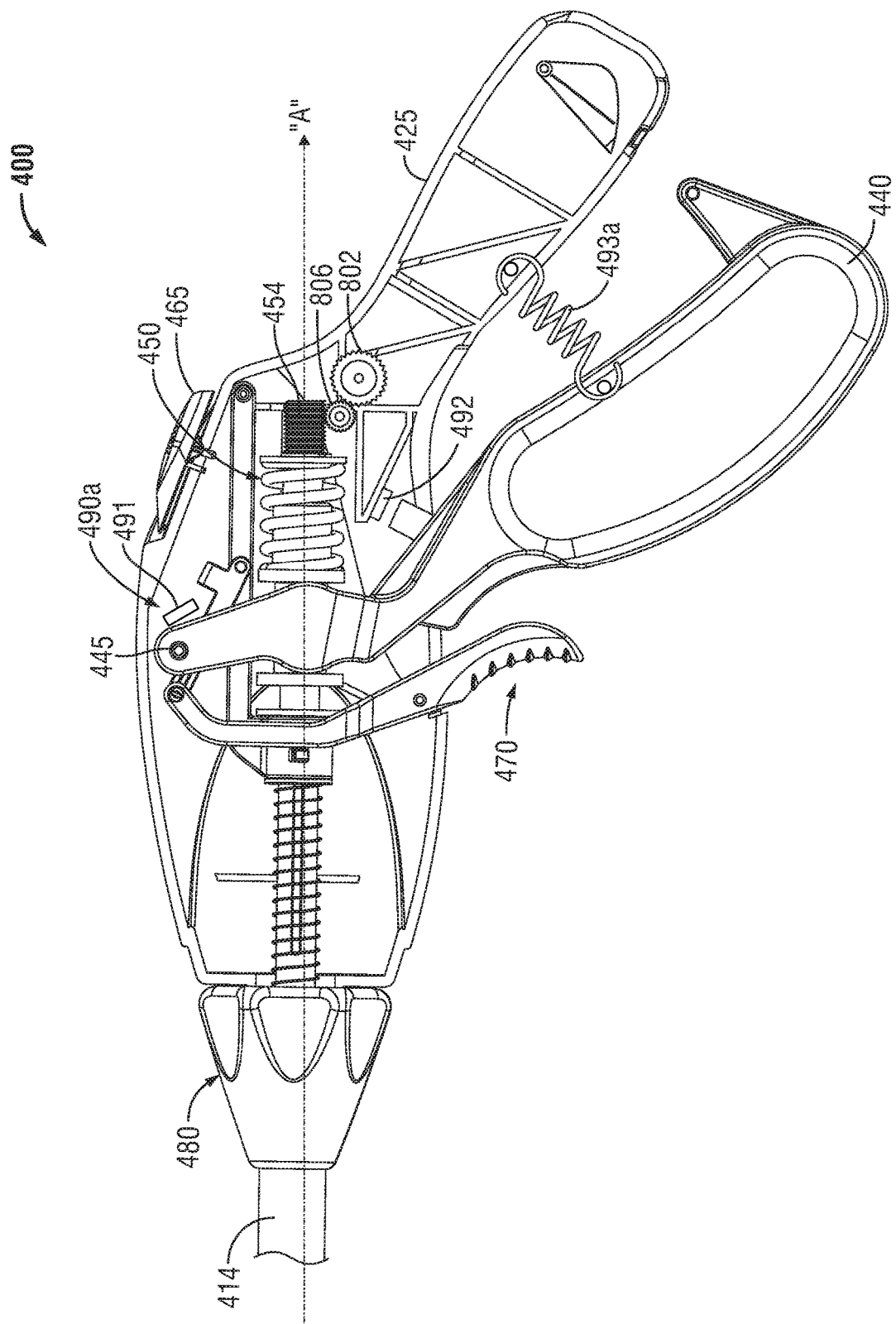
FIG. 2 is side view of the bipolar forceps of FIG. 1 with the internal working components of the forceps exposed in accordance with an embodiment of the present disclosure.
Figure 3:
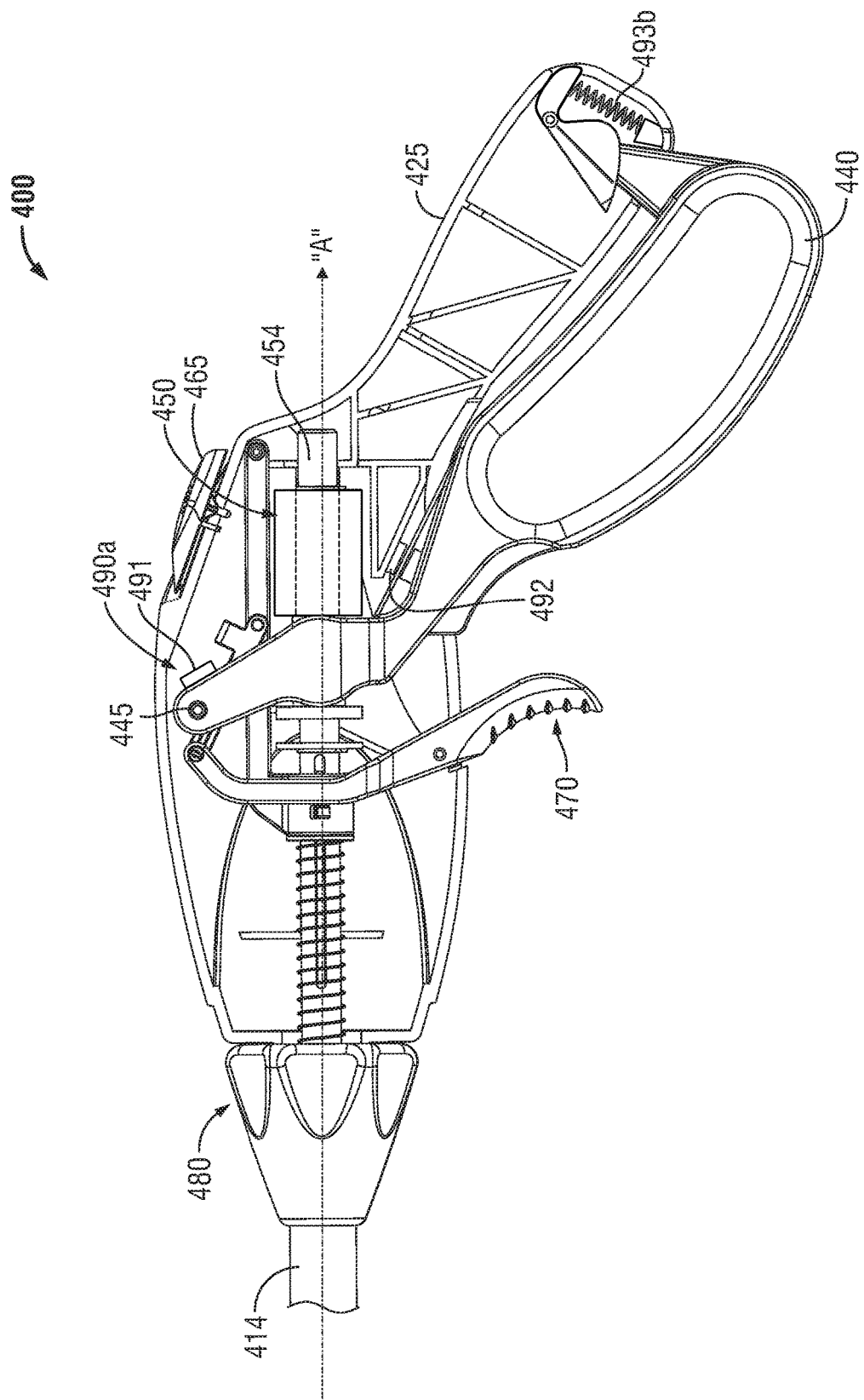
FIG. 3 is side view of the bipolar forceps of FIG. 2 with the internal working components of the forceps exposed in accordance with an embodiment of the present disclosure.

In FIGS. 1 through 3, an embodiment of a bipolar forceps 400 including a force-balance interface is shown for use with various surgical procedures. Forceps 400 generally includes a housing 420, a handle assembly 430, a rotating assembly 480, a trigger assembly 470, and an end-effector assembly 401. End-effector assembly 401 generally includes two jaw members 410 and 420 disposed in opposing relation relative to one another. Forceps 400 may include additional, fewer, or different components than shown in FIGS. 1 through 3, depending upon a particular purpose or to achieve a desired result.

Forceps 400 includes a shaft 412 having a distal end 416 configured to mechanically engage the end-effector assembly 401 and a proximal end 414 configured to mechanically engage the housing 420. Rotatable assembly 480 is operatively associated with the housing 420 and is rotatable approximately 180 degrees about a longitudinal axis "A-A" defined by the shaft 412. As shown in FIG. 1, the end-effector assembly 401 is rotatable about the longitudinal axis "A-A" through rotation, either manually or otherwise, of the rotatable assembly 480. One or more components of the bipolar forceps 400, e.g., the housing 420, the handle assembly 430, the rotatable assembly 480, the trigger assembly 470, and/or the end-effector assembly 401, may be adapted to mutually cooperate to grasp, seal and/or divide tissue, e.g., tubular vessels and vascular tissue (e.g., 720 shown in FIGS. 7 and 8).

End-effector assembly 401 may be configured as a unilateral assembly, i.e., the end-effector assembly 401 may include a stationary or fixed jaw member, e.g., 420, mounted in fixed relation to the shaft 412, and a moveable jaw member, e.g., 410, mounted about a pivot pin 403 coupled to the fixed jaw member. Alternatively, the forceps 410 may include a bilateral assembly, i.e., both jaw members 410 and 420 are moveable relative to one another. Jaw members 410 and 420 may be curved at various angles to facilitate manipulation of tissue and/or to provide enhanced line-of-sight for accessing targeted tissues.

In some embodiments, as shown in FIG. 1, forceps 400 includes an electrosurgical cable 415. Electrosurgical cable 415 may be formed from a suitable flexible, semi-rigid or rigid cable, and may connect directly to an electrosurgical power generating source 428. Electrosurgical power generating source 428 may be any generator suitable for use with electrosurgical devices, and may be configured to provide various frequencies of electromagnetic energy. Examples of electrosurgical generators that may be suitable for use as a source of electrosurgical energy include generators sold by Covidien Surgical Solutions of Boulder, Colo., e.g., Ligasure™ generator, FORCE EZ™ electrosurgical generator, FORCE FX™ electrosurgical generator, and FORCE TRIAD™ electrosurgical generator FORCE 1C™ generator, FORCE 2™ generator, SurgiStat™ II, or other generators which may perform different or enhanced functions. Forceps 400 may alternatively be configured as a battery-powered wireless instrument.

Handle assembly 430 includes a fixed handle 425 and a handle 440 that has a relatively fixed position. Handle 440 is preloaded with a positive force against a sensor 492 by a spring (e.g., spring 493a shown in FIG. 2, or spring 493b shown in FIG. 3). As seen in FIGS. 2 and 3, handle 440 is selectively movable to increase or decrease force applied to the sensor 492 above or below the preload. Powered force applicator 450 extends drive rod 454 in the direction "A" until the force of 450 against the jaw members 410 and 420 reaches a balance force. The balance force is equal and oppositely applied through the powered force applicator 450 against the handle 440 and results in reaction to bring the sensor 492 back to its preloaded condition. End-effector assembly 401 is configured to allow the jaw members 410 and 420 to move freely until, either, tissue is compressed between the inner surfaces (e.g., electrically-conductive sealing plates) of the jaw members 410 and 420, or tissue is extended on the outer surfaces of the jaw members 410 and 420. The resistance of the tissue is force transmitted back through to the sensor 454. The lever advantage is through the relative differences in the distance between the powered force applicator 450 and the hinge 445, the force sensor 492, and the user's grip location on the handle 440.

Figure 4:
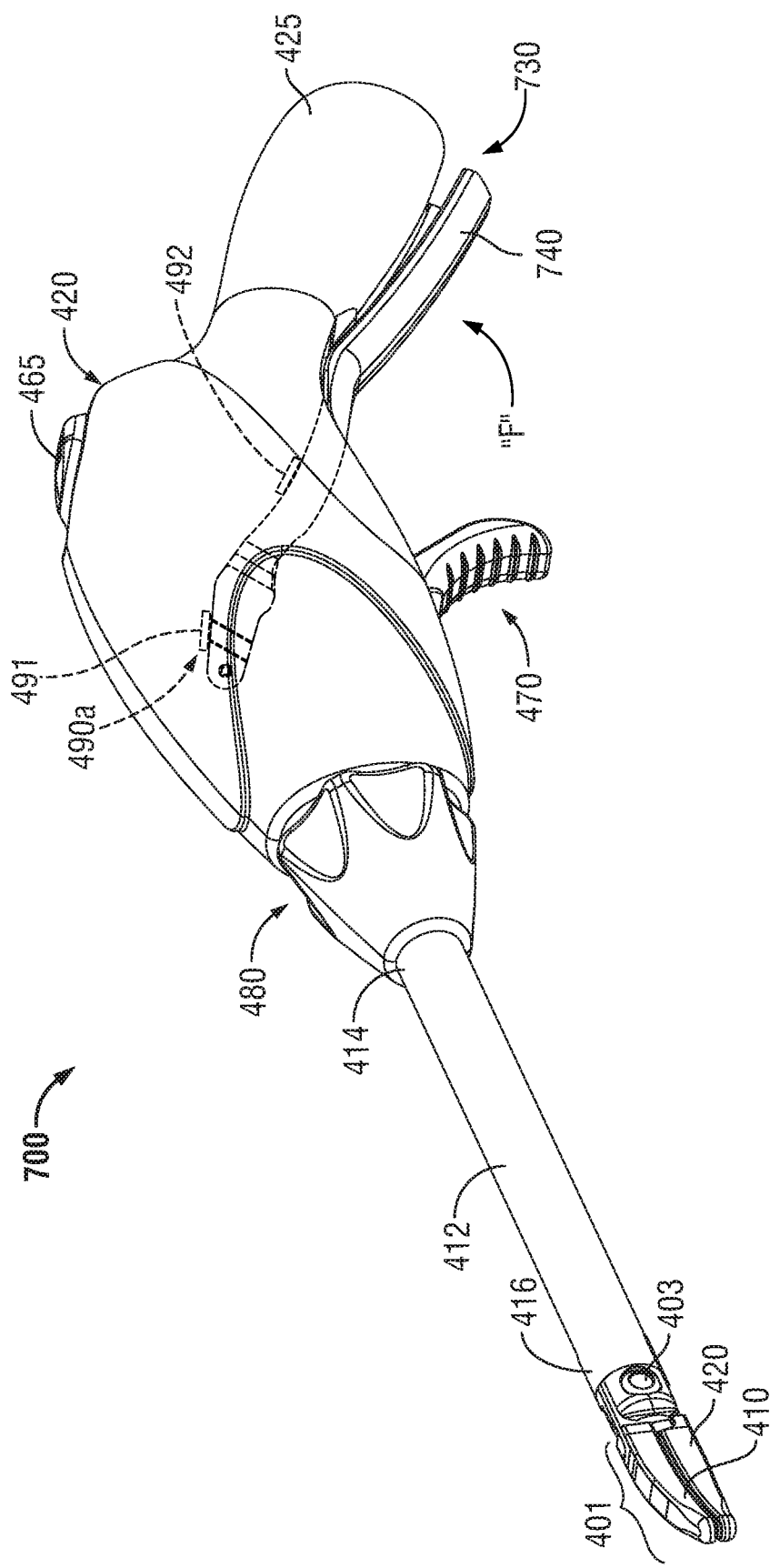
FIG. 4 is a perspective view, partially shown in phantom lines, of a bipolar forceps shown in a closed configuration and including a handle assembly and a force-balance interface in accordance with an embodiment of the present disclosure.

Forceps 400 includes a force-balance interface adapted to translate user-applied force exerted on the handle assembly 430 into the jaw members 410 and 420. In some embodiments, as shown in FIG. 4, the force-balance interface includes a first force-balance interface 490a (also referred to herein as a "force-balance handle interface 490a") and a second force-balance interface 490b (also referred to herein as a "force-balance jaw interface 490b"). Force-balance handle interface 490a includes one or more force sensors (e.g., two force sensors 491 and 492) disposed in association with the handle assembly 430, or component thereof (e.g., movable handle 440). Force sensors 491 and 492 may include any suitable device configured to generate an electrical signal indicative of the user-applied force exerted on the handle assembly 30. Force-balance jaw interface 490b includes one or more force sensors (e.g., force sensor 497) disposed in association with the end-effector assembly 101, or component thereof (e.g., jaw member 420).

In some embodiments, a piezoelectric or electromechanical force sensor may be utilized for the force sensor 491, the force sensor 492, and/or the force sensor 497. In some embodiments, the force sensor 491, 492 and/or 497 may be composed of a flex circuit. An example of a flexible circuit type sensor that may be suitable for use as the force sensor 491, 492 and/or 497 is commercially available under the trademark FlexiForce® offered by Tekscan of Boston, Mass. A variety of other force-sensing technologies such as load cells, piezoresistive, and capacitive sensors also may be utilized for the force sensor 491, 492 and/or 497.

Figure 5:
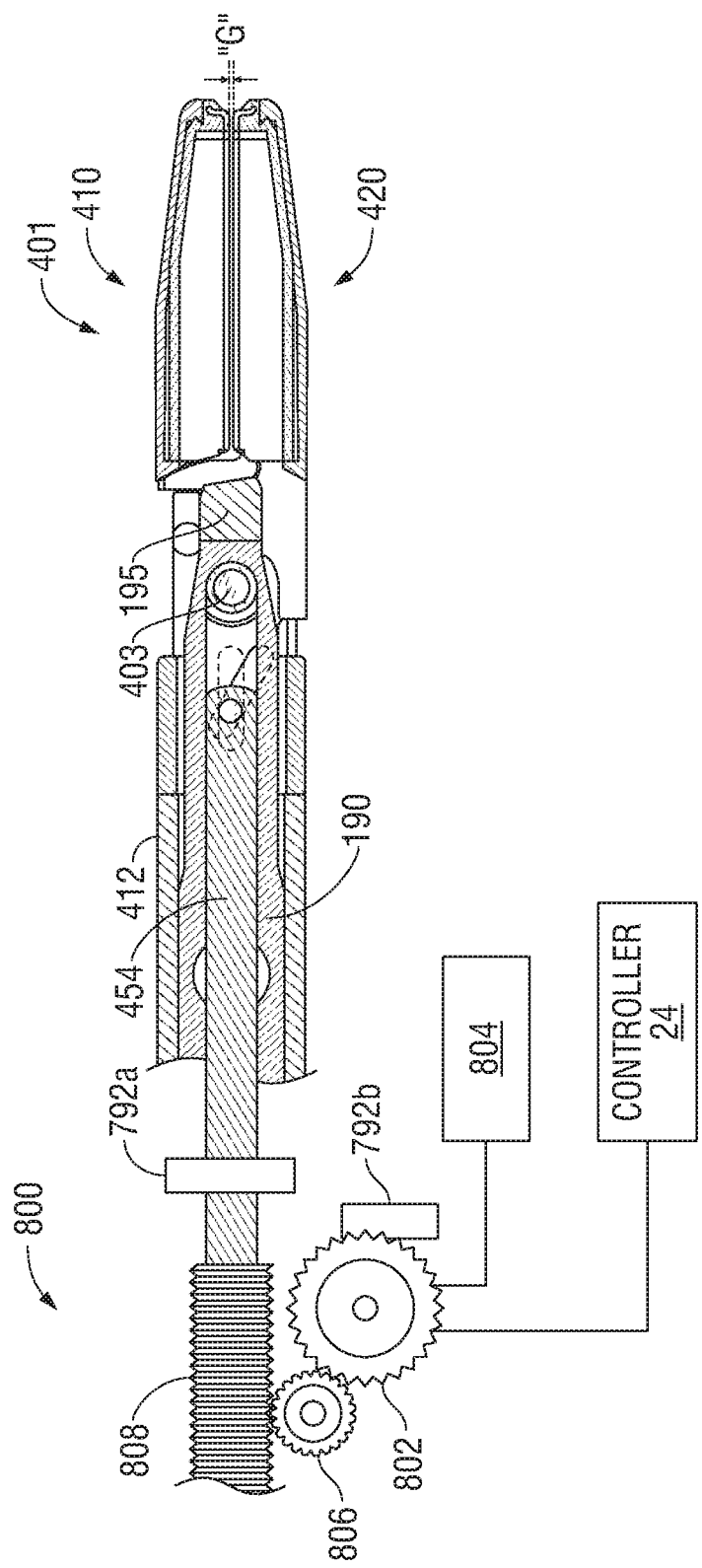
FIG. 5 is a side, partial internal view of the end-effector assembly of FIG. 1 shown with a schematically-illustrated force applicator in accordance with an embodiment of the present disclosure.
Figure 6:
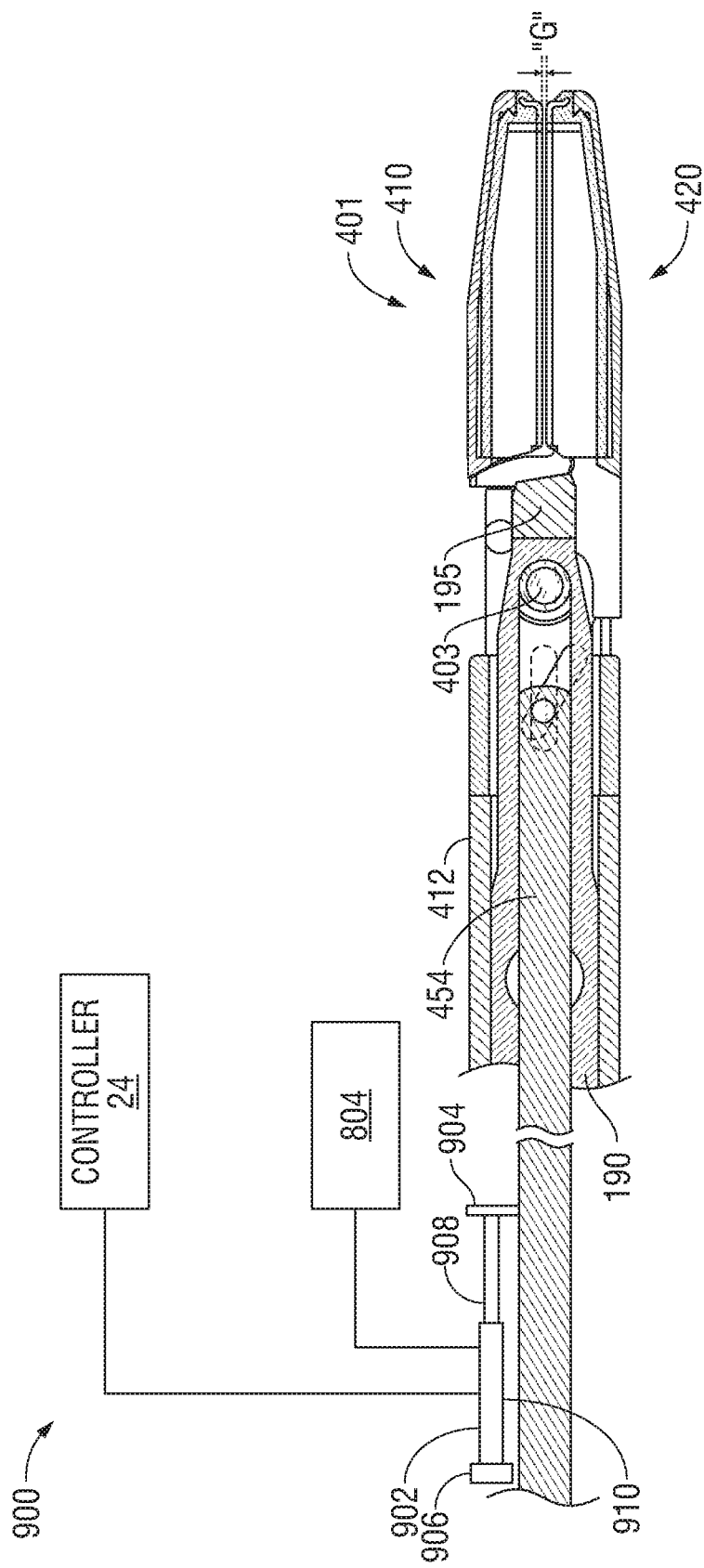
FIG. 6 is a side, partial internal view of the end-effector assembly of FIG. 1 shown with a schematically-illustrated pneumatic force applicator in accordance with another embodiment of the present disclosure.

Force sensor 491, 492 and/or 497 may be communicatively coupled to a controller (e.g., controller 24 shown in FIGS. 5 and 6). In some embodiments, the controller may be configured to control one or more operating parameters of the end-effector assembly 401 responsive, at least in part, to one or more electrical signals received from the force sensor 491, the force sensor 492, and/or the force sensor 497. In some embodiments, the controller may be communicatively-coupled to a force applicator and configured to control the rate of closure of the jaw members 410 ad 420, e.g., during activation, and/or control the compressive force (e.g., "F" shown in FIG. 7) exerted by the jaw members 410 and 420 and/or other operating parameters of the end-effector assembly 401 responsive, at least in part, to one or more electrical signals received from the force sensor 491, the force sensor 492, and/or the force sensor 497.

In FIG. 4, an embodiment of a bipolar forceps 700 is shown for use with various surgical procedures. Bipolar forceps 700 includes a handle assembly 730, which includes a first handle 725 and a second handle 740. Bipolar forceps 700 includes the force-balance interface of the bipolar forceps 400 (FIGS. 1 through 3), wherein the two force sensors 491 and 492 are disposed in association with the second handle 740. Bipolar forceps 700 is similar to the bipolar forceps 400 shown in FIGS. 1 through 3, except for the configuration of the handle assembly 730, and further description with respect to the same elements is omitted herein for brevity.

In some embodiments, the first handle 725 is integrally associated with the housing 420. Second handle 740 or portion thereof (e.g., grip portion) is formed of a resilient material. Second handle 740 may include one or more ergonomic enhancing elements to facilitate handling, e.g., scallops, protuberances, elastomeric material, etc. Responsive to user-applied force "F" exerted on the second handle 740, the force sensor 491 and/or the force sensor 492 generates one or more electrical signals indicative of the user-applied force "F". Based, at least in part, on one or more signals generated by the force sensor 491 and/or the force sensor 492, the controller (e.g., controller 24 shown in FIGS. 5 and 6) and/or other circuitry (not shown) may adjust one or more operating parameters associated with the end-effector assembly 401 and/or one or more operating parameters associated with the electrosurgical energy source 428.

FIG. 5 shows the shaft 12 and the end-effector assembly 401 of FIG. 1 operably associated with a knife 190, a drive rod 454, and a force applicator 800 in accordance with the present disclosure. Force applicator 800 generally includes an electric motor 802 powered by a power source 804, e.g., a stand-alone low-voltage DC source (e.g., battery) or an integrated low-voltage power source as part of the electrosurgical energy source (e.g., 428 shown in FIG. 1). Although the end-effector assembly 401 is shown, it is to be understood that other end-effector assembly configurations may be used, which may include additional, fewer, or different components than shown in FIG. 8.

Figure 8:
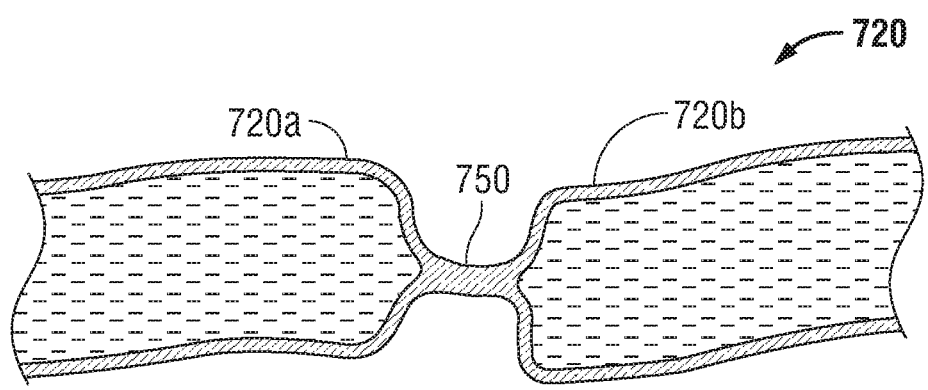
FIG. 8 is an enlarged, cross-sectional view of a tissue seal.

Drive rod 454 includes a threaded portion 808 disposed in mechanical communication with the motor 802. In some embodiments, as shown in FIG. 8, the motor 802 includes a gear box 806 that is mechanically coupled to the threaded portion 808 so that when the motor 802 is activated, the gears of the gear box 806 rotate and thereby longitudinally move the drive rod 454. Pulling the drive rod 454 proximally and moving the jaw members 410 and 420 apart, or pushing the drive rod 454 distally and moving the jaw members 410 and 420 together, is accomplished by varying the direction of rotation of the motor 802. The rate of closure of the jaw members 410 and 420 may be controlled by varying the gears within the gear box 806 and/or adjusting the power supplied to the motor 802, which, in turn, adjusts the rate of rotation and torque exerted on the drive rod 454.

Force applicator 800 is communicatively-coupled to a controller 24. Controller 24 may include any type of computing device, computational circuit, or any type of processor or processing circuit capable of executing a series of instructions that are stored in a memory (not shown) associated with the controller 24, where memory may be any device or medium that can store code and/or data. Functions of the controller 24 can be performed in hardware and/or software, as desired. In some embodiments, the controller 24 may be disposed in association with the housing, the handle assembly, or other component of the device (e.g., forceps 400 shown in FIG. 1, and forceps 700 shown in FIG. 4) or disposed in association with the electrosurgical energy source (e.g., 428 shown in FIG. 1).

Controller 24 may include logic, circuitry and/or code adapted to control the motor 802 responsive to one or more electrical signals received from one or more force sensors (e.g., force sensors 491, 492 and 497 shown in FIGS. 1 and 3). In some embodiments, the controller 24 may be configured to receive user-inputs from one or more user-input devices, including without limitation, a joystick, trackball, touchscreen, and/or other user-input device. Controller 24 may be configured to automatically adjust the operating parameters of the motor 802 based on user input and/or electrical signals received from one or more force sensors associated with any one of the above-described force-balance interfaces.

In some embodiments, the controller 24 may additionally, or alternatively, be configured to electrically, mechanically or electro-mechanically adjust the distance the stop members (not shown) project by retracting or extending the stop members from the sealing plate. As a result, the gap distance "G" is adjusted by changing the distance that the stop members project from the sealing plate.

In some embodiments, the presently-disclosed forceps (e.g., forceps 400 shown in FIG. 1, and forceps 700 shown in FIG. 4) may be configured to shift to an absolute force sensor 792a or 792b (FIG. 5), e.g., located separately from the force sensors of the force-balance interface, and drive to a predetermined force (e.g., "F" shown in FIG. 7) and/or pressure (e.g., between about 3 kg/cm$^2$ to about 16 kg/cm$^2$) applied between the opposing jaw members, e.g., before and during activation of energy, wherein the motor 802 is prevented from reversing when the user initiates a seal cycle.

FIG. 6 shows the shaft 12 and the end-effector assembly 401 of FIG. 1 operably associated with a knife 190, a drive rod 454, and a force applicator 900 in accordance with the present disclosure. Force applicator 900 includes a linear actuator 902 powered by the power source 804. The linear actuator 902 includes a housing cylinder 910 and a shaft 908.

Figure 9:
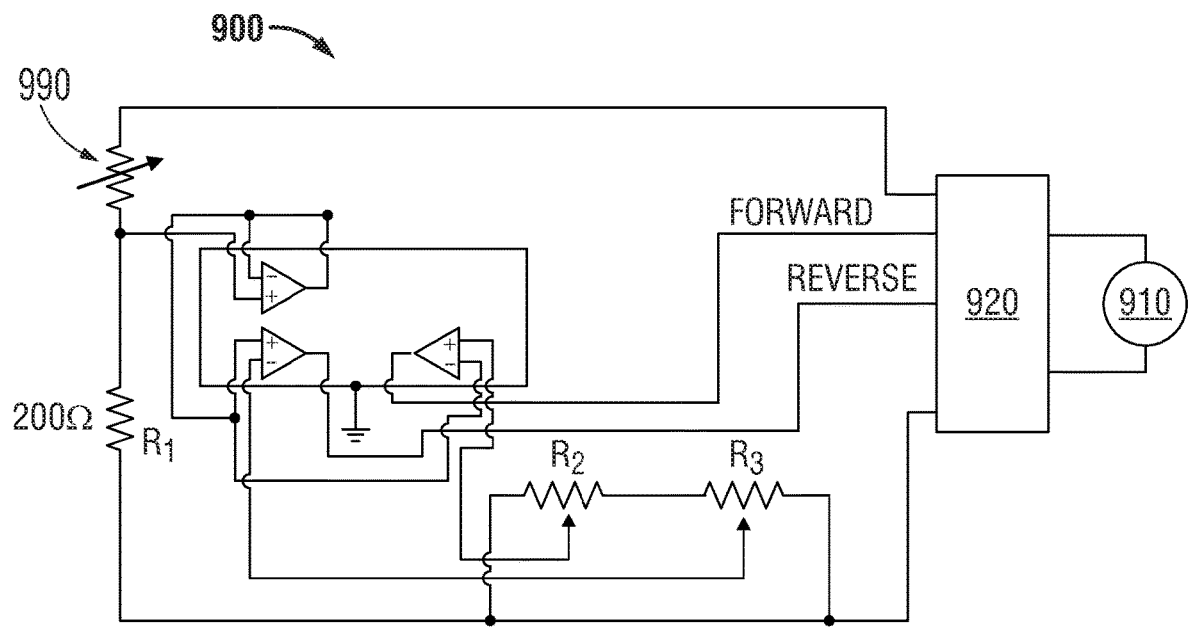
FIG. 9 is a schematic diagram of a force-balance circuit in accordance with the present disclosure.
Figure 10:
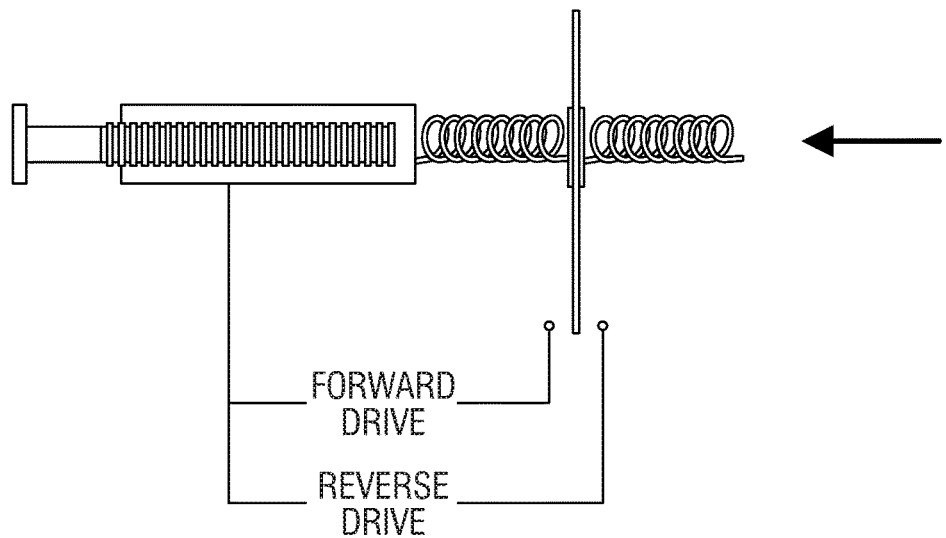
FIG. 10 is a diagrammatic representation of a force-balance interface in accordance with the present disclosure.

As seen in FIG. 9, the shaft 908 is mechanically coupled to the drive rod 454 at an interface 904. In some embodiments, the housing cylinder 910 of the linear actuator 902 is mechanically coupled to the interior wall of the housing of the forceps (e.g., housing 420 shown in FIGS. 1 and 4) at an interface 906. Linear actuator 902 moves the drive rod 454 in a longitudinal direction proximally or distally by expanding or contracting, respectively, between the interfaces 904 and 906. Linear actuator 902 may include an electric motor or a pneumatic or hydraulic cylinder that extends or retracts the shaft 908. Those skilled in the art will readily appreciate that if the linear actuator 902 is pneumatic, the shaft 908 may be part of the pneumatic cylinder. Power source 804 is connected to the linear actuator 902 and provides electrical power thereto. In some embodiments, the controller 24 controls the operating parameters of the linear actuator 902, either, directly, or by controlling the power source 804, e.g., based on user input and/or electrical signals received from one or more force sensors associated with any one of the above-described force-balance interfaces.

Figure 7:
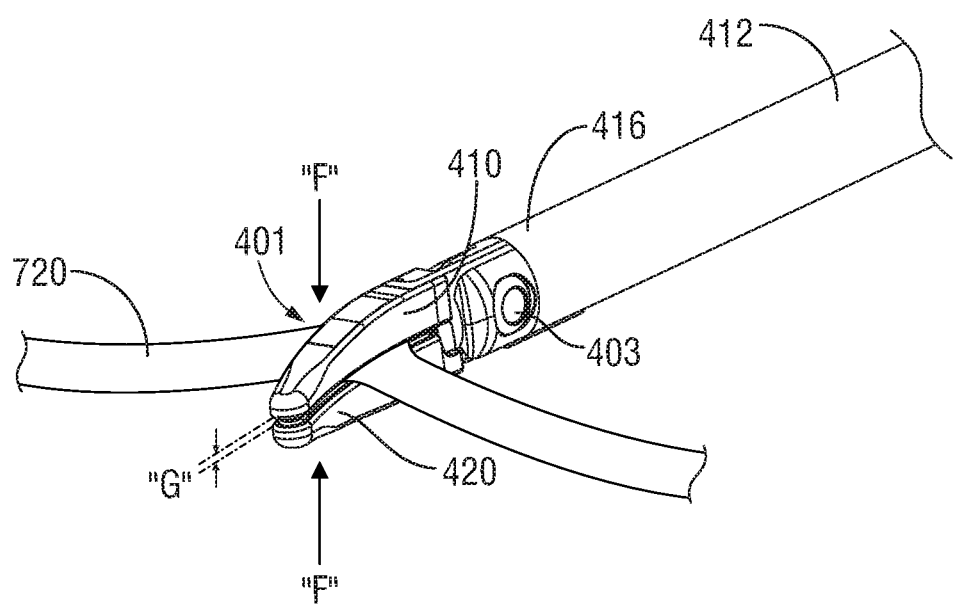
FIG. 7 is an enlarged, rear perspective view of the end-effector assembly of FIG. 1 shown grasping tissue.

Turning now to FIG. 7, the end-effector assembly 401 of an embodiment of the above-described forceps with a force-balance interface is shown during a sealing procedure. In FIG. 7, the end-effector assembly 401 is shown grasping tissue 720. In some embodiments, the end-effector assembly 401 may include a gap distance "G" between opposing sealing surfaces during sealing, e.g., in the range from about 0.001 inches to about 0.006 inches. In some embodiments, the end-effector assembly 401 includes a gap distance "G" between opposing sealing surfaces during sealing that ranges from about 0.002 to about 0.003 inches.

As energy is selectively transferred to the end-effector assembly 401 and applied to the opposing jaw members 410 and 420 and through the tissue 720 held therebetween, a tissue seal 750 forms isolating two tissue halves 720a and 720b (see FIG. 8). In some embodiments, a knife assembly (e.g., 190 shown in FIG. 5), e.g., activated via the trigger assembly 470 (FIG. 1), progressively and selectively divides the tissue 720 along a tissue plane in a precise manner to divide the tissue 720 into two sealed halves (not shown).

Once the tissue 720 is divided into tissue halves, the jaw members 410 and 420 may be opened by re-initiation or re-grasping of the handle 440.

In FIG. 9, a force-balance circuit 900 is shown in accordance with the present disclosure. Force-balance circuit 900 generally includes a force applicator 910, e.g., a motor, and an H-bridge 920. An op amp circuit is used as a conditioner for the resistive-element force sensor 990. The voltage from the force sensor 990 is biased by a resistor and two potentiometers R2 and R3 provide reference voltages to two comparators, which may be used to advance the motor 910 drive forward or in reverse. The two comparators provide output to the H-bridge 920. The first comparator provides an output signal when voltage from force sensor 990 indicates increasing forward motion of the force applicator motor 910 and the second comparator provides an output signal when the voltage indicates reversing the force applicator motor 910 to reduce force delivered through the shaft to the jaw members 410 and 420. The two reference voltages for the two comparator may be offset from each other such that only one comparator outputs to the H-bridge 920 at a time. Generally this provides a dead zone when the force of the handle 440 and force applicator are matched and the motor 910 is off. One can appreciate the simplicity and low cost of the circuit and its adequacy for control and that an equivalent variable output circuit could be constructed to perform similar function at greater complexity.

FIG. 11 is a diagrammatic representation of a force-balance interface in accordance with the present disclosure. Increasing the input force (illustratively depicted by the arrowed line in FIG. 11) compresses the two springs, thereby moving the sensor plate to the "forward drive" position. The motor extends the linear actuator until the springs are oppositely compressed, thereby returning the sensor plate to a neutral position. Decreasing the input force has the opposite effect, e.g., causing the sensor plate to move to the "reverse drive" position.

The above-described bipolar forceps embodiments include a force-balance interface and may be suitable for use in a variety of procedures and operations. The above-described end-effector embodiments may utilize both mechanical clamping action and electrical energy to effect hemostasis by heating tissue and blood vessels to coagulate, cauterize, cut and/or seal tissue. The jaw members may be either unilateral or bilateral. The above-described bipolar forceps embodiments that include a force-balance interface may be suitable for utilization with endoscopic surgical procedures and/or hand-assisted, endoscopic and laparoscopic surgical procedures. The above-described bipolar forceps embodiments may be suitable for utilization in open surgical applications.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A surgical instrument, comprising:
   a housing;
   a shaft extending distally from the housing;
   an end effector disposed adjacent a distal portion of the shaft and including a first jaw member and a second jaw member, at least one of the first jaw member or the second jaw member movable relative to the other jaw member;
   a handle assembly including a movable handle, wherein actuation of the movable handle causes the at least one of the first jaw member or the second jaw member to move relative to the other jaw member; and
   a force-balance interface configured to translate a multiple of a user-applied force exerted on the handle assembly into at least one of the first jaw member or the second jaw member, the force-balance interface including at least one force sensor configured to be contacted by the movable handle during a range of motion thereof,
   wherein the at least one jaw member moves relative to the other jaw member prior to the movable handle contacting the at least one force sensor.

2. The surgical instrument according to claim 1, wherein the handle assembly includes the movable handle and a fixed handle.

3. The surgical instrument according to claim 2, wherein the movable handle is pivotable relative to the fixed handle.

4. The surgical instrument according to claim 1, wherein the movable handle is movable between a first position where the movable handle is free from contact with the at least one force sensor, and a second position where the movable handle is in contact with the at least one force sensor.

5. The surgical instrument according to claim 1, further including a drive rod slidably disposed at least partially within the shaft.

6. The surgical instrument according to claim 5, further including a force applicator coupled to the drive rod, wherein the force applicator and the drive rod mechanically communicate to impart movement to the at least one jaw member.

7. The surgical instrument according to claim 6, further including a controller communicatively-coupled to the at least one force sensor and communicatively-coupled to the force applicator.

8. The surgical instrument according to claim 7, wherein the force applicator includes an electric motor.

9. The surgical instrument according to claim 7, wherein the force applicator includes a linear actuator.

10. The surgical instrument according to claim 9, wherein the controller is configured to control at least one operating parameter of the linear actuator based on at least one signal received from the at least one force sensor.

11. The surgical instrument according to claim 1, wherein the at least one force sensor is configured to transmit a signal indicative of the user-applied force exerted on the handle assembly.

12. The surgical instrument according to claim 11, further including a controller communicatively-coupled to the at least one force sensor.

13. The surgical instrument according to claim 1, wherein the movable handle is preloaded with a positive force against the at least one force sensor by a spring.

14. A surgical instrument, comprising:
   a housing;
   a shaft extending distally from the housing;
   an end effector disposed adjacent a distal portion of the shaft and including a first jaw member and a second jaw member, at least one of the first jaw member or the second jaw member movable relative to the other jaw member;

an actuator, wherein actuation of the actuator causes the at least one jaw member to move relative to the other jaw member; and at least one force sensor configured to be engaged by the actuator, wherein the at least one jaw member moves relative to the other jaw member prior to the actuator engaging the at least one force sensor.

15. The surgical instrument according to claim 14, wherein the actuator is movable between a first position where the actuator is free from contact with the at least one force sensor, and a second position where the actuator is in contact with the at least one force sensor.

16. The surgical instrument according to claim 14, further including a drive rod slidably disposed at least partially within the shaft.

17. The surgical instrument according to claim 16, further including a force applicator coupled to the drive rod, wherein the force applicator and the drive rod mechanically communicate to impart movement to the at least one jaw member.

18. The surgical instrument according to claim 14, wherein the actuator is preloaded with a positive force against the at least one force sensor by a spring.

19. The surgical instrument according to claim 14, wherein the at least one sensor is included on a first force-balance interface, the first force-balance interface configured to translate a multiple of a user-applied force exerted on the actuator into at least one of the first jaw member or the second jaw member.

* * * * *